(12) United States Patent
Nordstrom et al.

(10) Patent No.: US 7,162,288 B2
(45) Date of Patent: Jan. 9, 2007

(54) TECHNIQUES FOR DETECTING HEART PULSES AND REDUCING POWER CONSUMPTION IN SENSORS

(75) Inventors: Brad Nordstrom, Alameda, CA (US); William Shea, Livermore, CA (US); Ethan Petersen, Castro Valley, CA (US)

(73) Assignee: Nellcor Purtain Bennett Incorporated, Pleasanton, CA (US)

( * ) Notice: Subject to any disclaimer, the term of this patent is extended or adjusted under 35 U.S.C. 154(b) by 375 days.

(21) Appl. No.: 10/787,851

(22) Filed: Feb. 25, 2004

(65) Prior Publication Data

US 2005/0187446 A1 Aug. 25, 2005

(51) Int. Cl.
*A61B 5/00* (2006.01)
(52) U.S. Cl. .................................... 600/323
(58) Field of Classification Search ............... 600/300, 600/309, 322, 323, 324; 356/41; 359/239
See application file for complete search history.

(56) References Cited

U.S. PATENT DOCUMENTS

| | | | |
|---|---|---|---|
| 3,721,813 A | 3/1973 | Condon et al. | |
| 4,802,486 A | 2/1989 | Goodman et al. | |
| 4,911,167 A | 3/1990 | Corenman et al. | |
| 4,928,692 A | 5/1990 | Goodman et al. | |
| 4,934,372 A | 6/1990 | Corenman et al. | |
| 5,351,685 A | 10/1994 | Potratz | |
| 5,368,026 A | 11/1994 | Swedlow et al. | |
| 5,662,106 A | 9/1997 | Swedlow et al. | |
| 5,713,355 A | 2/1998 | Richardson et al. | |
| 5,746,697 A | 5/1998 | Swedlow et al. | |
| 5,803,910 A | 9/1998 | Potratz | |
| 5,885,213 A | 3/1999 | Richardson et al. | |
| 5,921,921 A | 7/1999 | Potratz et al. | |
| 5,924,979 A | 7/1999 | Swedlow et al. | |
| 6,163,715 A | 12/2000 | Larsen et al. | |
| 6,226,539 B1 | 5/2001 | Potratz | |
| 6,261,236 B1 | 7/2001 | Grimblatov | |
| 6,356,774 B1 | 3/2002 | Bernstein et al. | |
| 6,393,311 B1 | 5/2002 | Edgar et al. | |
| 6,863,652 B1 * | 3/2005 | Huang et al. | ............... 600/300 |

FOREIGN PATENT DOCUMENTS

| | | |
|---|---|---|
| EP | 0314331 A1 | 5/1989 |
| EP | 0875199 A1 | 11/1998 |

* cited by examiner

*Primary Examiner*—Eric Winakur
*Assistant Examiner*—Etsub D. Berhanu
(74) *Attorney, Agent, or Firm*—Fletcher Yoder PC

(57) ABSTRACT

Low power techniques for sensing cardiac pulses in a signal from a sensor are provided. A pulse detection block senses the sensor signal and determines its signal-to-noise ratio. After comparing the signal-to-noise ratio to a threshold, the drive current of light emitting elements in the sensor is dynamically adjusted to reduce power consumption while maintaining the signal-to-noise ratio at an adequate level. The signal component of the sensor signal can be measured by identifying systolic transitions. The systolic transitions are detected using a maximum and minimum derivative averaging scheme. The moving minimum and the moving maximum are compared to the scaled sum of the moving minimum and moving maximum to identify the systolic transitions. Once the signal component has been identified, the signal component is compared to a noise component to calculate the signal-to-noise ratio.

16 Claims, 3 Drawing Sheets

TECHNIQUES FOR DETECTING HEART PULSES AND REDUCING POWER CONSUMPTION IN SENSORS

BACKGROUND OF THE INVENTION

The present invention relates to techniques for detecting heart pulses and reducing power consumption in sensors and oximeter systems, and more particularly, to techniques for distinguishing heart pulses in a sensor signal from noise and adjusting drive current provided to light emitting elements in response to a signal-to-noise ratio of the pulse in order to reduce power consumption.

Pulse oximetry is a technology that is typically used to measure various blood chemistry characteristics including, but not limited to, the blood-oxygen saturation of hemoglobin in arterial blood, the volume of individual blood pulsations supplying the tissue, and the rate of blood pulsations corresponding to each heartbeat of a patient.

Measurement of these characteristics has been accomplished by use of a non-invasive sensor. The sensor has a light source such as a light emitting diode (LED) that scatters light through a portion of the patient's tissue where blood perfuses the tissue. The sensor also has a photodetector that photoelectrically senses the absorption of light at various wavelengths in the tissue. The photodetector generates a pulse oximeter signal that indicates the amount of light absorbed by the blood. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption.

For measuring blood oxygen level, oximeter sensors typically have a light source that is adapted to generate light of at least two different wavelengths, and with photodetectors sensitive to these wavelengths, in accordance with known techniques for measuring blood oxygen saturation. A typical pulse oximeter will alternately illuminate the patient with red and infrared light using two LEDs to obtain two different detector signals.

The pulse oximeter signal generated by the photodetector usually contains components of noise introduced by the electronics of the oximeter, by the patient, and by the environment. Noisy signals have a low signal-to-noise ratio. A pulse oximeter cannot accurately identify the blood oxygen saturation when the signal-to-noise ratio of the pulse oximeter signal is too low.

To improve the signal-to-noise ratio of the pulse oximeter signal, a pulse oximeter system will typically drive the LEDs with a large amount of current. A servo in the pulse oximeter will typically drive as much current as possible through the LEDs without causing the oximeter to be over-ranged (i.e., driven to full rail). The large drive current causes the LEDs to generate more light and to consume more power. Because the photodetector is able to sense more of the light from the LEDs, the signal-to-noise ratio of the pulse oximeter signal is higher.

Increasing the drive current of the LEDs to improve the signal-to-noise ratio of the pulse oximeter signal causes the system to consume an undesirably large amount of power. The large amount of power consumption can be a problem for oximeter systems that are battery operated.

It would therefore be desirable to provide pulse oximeter systems that consume less power without negatively compromising the signal-to-noise ratio of the pulse oximeter signal.

BRIEF SUMMARY OF THE INVENTION

The present invention provides CPU cycle efficient techniques for sensing heart pulses in a signal from a sensor. The sensor signal can be, for example, a pulse oximeter signal generated by a photodetector in a pulse oximeter sensor. The signal component of the sensor signal is measured by identifying potential systolic transitions of the cardiac cycle. The systolic transitions are detected using a derivative averaging scheme. The moving minimum and the moving maximum of the average derivative are compared to a scaled sum of the minimum and maximum to identify the systolic transitions. The systolic transitions correspond to a signal component of the sensor signal. The signal component is compared to a noise component to determine the signal-to-noise ratio of the signal.

The present invention also provides techniques for reducing power consumption in a sensor. After the signal-to-noise ratio of the pulse oximeter has been determined, the signal-to-noise ratio is compared to a threshold. In response to the output of the comparison, the drive current of light emitting elements in the sensor is dynamically adjusted to reduce power consumption and to maintain the signal-to-noise ratio at an adequate level for signal processing.

The present invention also provides techniques for sensing and adjusting the gain of a transimpedance amplifier to reduce the effect of ambient noise in a sensor. A gain control feedback loop senses the magnitude of the sensor signal when the light emitting elements are off. The gain control loop can include this information to effectively control the gain of the transimpedance amplifier.

For a further understanding of the nature and advantages of the invention, reference should be made to the following description taken in conjunction with the accompanying drawings.

DETAILED DESCRIPTION OF THE INVENTION

Figure 1:
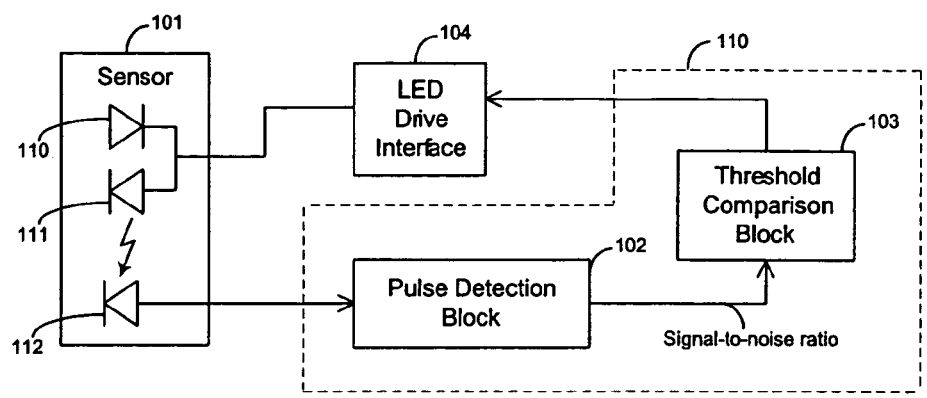
FIG. 1 illustrates a block diagram of a pulse oximeter system with reduced power consumption according to an embodiment of the present invention.

The techniques of the present invention can be used in the context of a pulse oximeter system. A pulse oximeter system receives a pulse oximeter signal from a photodetector in a pulse oximeter sensor. FIG. 1 illustrates a block diagram of pulse oximeter system according to an embodiment of the present invention. The pulse oximeter system includes an oximeter sensor 101.

An oximeter sensor of the present invention can utilize any suitable number of light emitting elements. For example, a sensor of the present invention can have 1, 2, 3, or 4 light emitting elements. In the example of FIG. 1, sensor 101 has two LEDs 110 and 111 that emit two different wavelengths of light.

Sensor 101 also includes photodetector 112 that senses light from LEDs 110 and 111 after the light has passed through the patient's tissue. The pulse oximeter system also includes feedback loop circuitry 110 and LED drive interface 104. Feedback loop circuitry 110 includes pulse detection block 102 and threshold comparison block 103.

Photodetector 112 transmits the pulse oximeter signal to pulse detection block 102. Pulse detection block 102 has a servo that measures the signal component of the pulse oximeter signal by identifying the systolic transitions. The pulse detection block 102 and the threshold comparison block 103 form a feedback loop 110 around the sensor to control the drive current of the LEDs and the signal-to-noise ratio of the pulse oximeter signal, as will be discussed in detail below.

A cardiac pulse can be divided into a diastolic and systolic period. The systolic period is typically characterized by a rapid change in value due to the contraction of the heart. The diastolic period is typically characterized by a gradual change in value, due to the relaxation and refilling of the heart chambers.

Systolic transitions in the pulse oximeter signal are detected using a three step maximum and minimum derivative averaging scheme, which is discussed in further detail below. Qualification routines are then used to filter out false positives. The resulting data contains the systolic transitions separated from the non-systolic periods in the pulse oximeter signal.

Pulse detection block 102 then compares the amplitude of the systolic portion of the pulse oximeter signal to a noise component to generate a value for the signal-to-noise ratio of the pulse oximeter signal. Subsequently, threshold comparison block 103 compares this signal-to-noise ratio to a threshold level to determine whether the signal-to-noise ratio is high enough such that the pulse oximeter signal can be used to accurately calculate pulse rate and oxygen saturation. Too much noise obscures the pulse rate and oxygen saturation information in the signal. Noise can degrade the signal to the point that it cannot be used to accurately calculate pulse rate or oxygen saturation.

Threshold comparison block 103 preferably contains two hysteretic threshold levels. In this embodiment, threshold comparison block 103 senses whether the signal-to-noise ratio is greater than a maximum threshold level or less than a minimum threshold level. As an example, the maximum threshold level can represent a signal-to-noise ratio of 128:1, and the minimum threshold level can represent a signal-to-noise ratio of 8:1. These are merely two examples of thresholds levels. They are not intended to limit the scope of the present invention. Prior art oximeter systems, for example, operate at a signal-to-noise ratio of 10,000:1 or higher, because they drive the LEDs as bright as possible.

If the signal-to-noise ratio is greater than the maximum threshold level, threshold comparison block 103 sends a signal to LED drive interface 104 to reduce the LED current. Based on the value of the signal-to-noise ratio, threshold comparison block 103 can determine how much the LED drive current needs to be reduced to decrease the signal-to-noise ratio while maintaining the signal level within the minimum and maximum threshold levels. LED drive interface 104 responds by decreasing the LED drive current to the value indicated by threshold comparison block 103.

The feedback loop continuously monitors the signal-to-noise ratio of the pulse oximeter signal and dynamically adjusts the LED drive current and subsequent system gain until the signal-to-noise ratio is less than the maximum threshold. The oximeter system saves power by substantially reducing the LED drive current (relative to prior art systems), while maintaining the signal-to-noise ratio of the pulse oximeter signal within an acceptable range.

The signal-to-noise ratio can also drop too low for a number of reasons. For example, the noise in the pulse oximeter may increase, or the strength of the signal component may decrease if the blood oxygen saturation of the patient decreases. In any event, the system of FIG. 1 senses when the magnitude of the pulse oximeter signal is too low and increases the LED drive current accordingly.

If the signal-to-noise ratio is less than the minimum threshold level, threshold comparison block 103 sends a signal to LED drive interface 104 to increase the LED current. Based on the value of the signal-to-noise ratio, the threshold comparison can determine how much the LED drive current needs to be increased to increase the signal-to-noise ratio while maintaining the signal within the minimum and maximum threshold levels. LED drive interface 104 responds by increasing the LED drive current to the value indicated by the threshold comparison system.

The feedback loop continuously monitors the signal-to-noise ratio of the pulse oximeter signal and dynamically adjusts the LED drive current until the signal-to-noise ratio is greater than the minimum threshold level. The minimum threshold indicates a minimum allowable value for the signal-to-noise ratio for which the pulse rate and the oxygen saturation can be accurately calculated.

If the signal-to-noise ratio falls between the maximum and minimum threshold levels, the oximeter system maintains the LED drive current at a stable value. The oximeter system maintains equilibrium until the signal-to-noise ratio of the pulse oximeter signal moves outside the range of the thresholds. Thus, an oximeter system of the present invention contains a dynamic feedback loop as shown in FIG. 1. The dynamic feedback loop automatically adjusts the drive current of the LEDs to reduce power consumption in the sensor and to maintain the signal-to-noise ratio at an acceptable level for the purpose of accurately calculating blood oxygen saturation levels.

According to a preferred embodiment of the present invention, the hardware for the servo in pulse detection block 102 maintains a predictable relationship between the power that LED drive 104 attempts to the drive the LEDs at and the radiated output power actually generated by the LEDs. By providing a predictable relationship between the input and output power, the feedback loop is more likely to acquire the oxygen saturation from the pulse oximeter signal in significantly less time, requiring less executions of the servo.

As the gain of the pulse oximeter signal is increased, the signal component generally increases faster than the noise component (at least to a point below the highest gain settings). The effect that increasing the gain of the pulse oximeter signal has on the signal-to-noise ratio in a particular system should be understood. Certain combinations of gain may cause more noise to be present in the pulse oximeter signal. Therefore, the gain stages in the pulse detection block preferably take advantage of characteristics of the gain-to-noise variability.

For example, the signal from the photodetector that is sampled using an analog-to-digital converter is fed into a gain block. The gain block includes several gain stages to achieve a known response. The noise is measured at each of the gain stages, and then stored for later use to calculate the signal-to-noise ratio.

Techniques for identifying the systolic portions of a pulse oximeter signal generated by an oximeter sensor are now discussed. The systole identification of the present invention uses a three step maximum and minimum derivative averaging scheme in order to detect cardiac systolic events.

Figure 2:
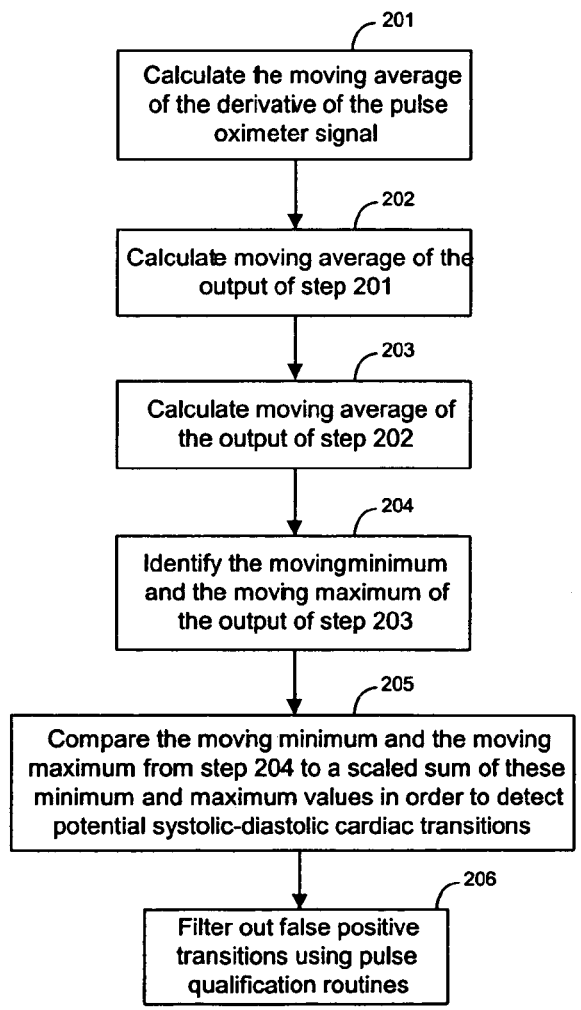
FIG. 2 is a flow chart that illustrates a process for identifying the systolic period of a pulse oximeter signal according to an embodiment of the present invention.

FIG. 2 illustrates one method for identifying the systolic period of a pulse oximeter signal. In the first step 201, the moving average of the derivative of the pulse oximeter signal is found. In the second step 202, the moving average of the output of the first step 201 is found. In the third step 203, the moving average of the output of the second step 202 is found.

Next, the moving maximum and the moving minimum of the output of the third step is found at step 204. At step 205, systole transitions are detected by comparing this moving minimum and moving maximum to a scaled sum of the moving minimum and maximum. For example, the scaled sum of the moving minimum and maximum values can be a fractional sum of the minimum and maximum moving averages.

When the minimum output of step 204 becomes less than a fractional sum of the maximum and minimum moving averages, the system determines that the pulse oximeter signal is entering systole. When the minimum output of step 204 becomes more than a fractional sum of the maximum and minimum moving averages, the system determines that pulse oximeter signal is exiting systole.

The two predetermined fractional sums can be selected to be any suitable values. As a specific example, the system can determine that the pulse oximeter signal is entering systole when the minimum derivative output becomes less than $1/16$ the sum of the minimum and maximum moving averages of the third stage. As another example, the system can determine that the pulse oximeter signal is exiting systole when the minimum derivative output becomes more than $1/8$ the sum of the maximum and minimum moving averages of the third stage. These two examples are not intended to limit the scope of the present invention. Many other fractional values can also be used to identify systole transitions.

These techniques of the present invention can detect and qualify pulses using CPU, RAM, and ROM efficient algorithms. Minimal processor resources are required to perform oximetry calculations with a comparable level of saturation and pulse rate performance as prior art oximeter technology.

Figure 3A:
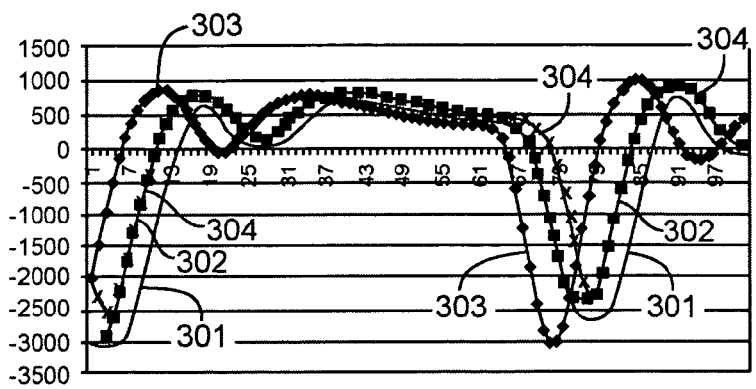
FIGS. 3A–3C are graphs that illustrates how systolic transitions are identified in pulse oximeter signals according to embodiments of the present invention.

Example waveforms for the results of these calculations are shown in FIG. 3A. Waveform 303 is an example of the derivative of a pulse oximeter signal. Waveforms 301 and 304 are examples of the minimum and maximum moving average of the pulse oximeter signal, respectively. Waveform 302 is an example of the output signal of the three-step moving average.

The output of the moving average is a smoothed and delayed version of the derivative of the pulse oximeter signal. The minimum output tracks the negative-going trends and lags the positive-going trends. The maximum output tracks the positive-going trends and lags the negative-going trends. These relationships are key to detecting potential systolic cardiac periods.

Figure 3B:
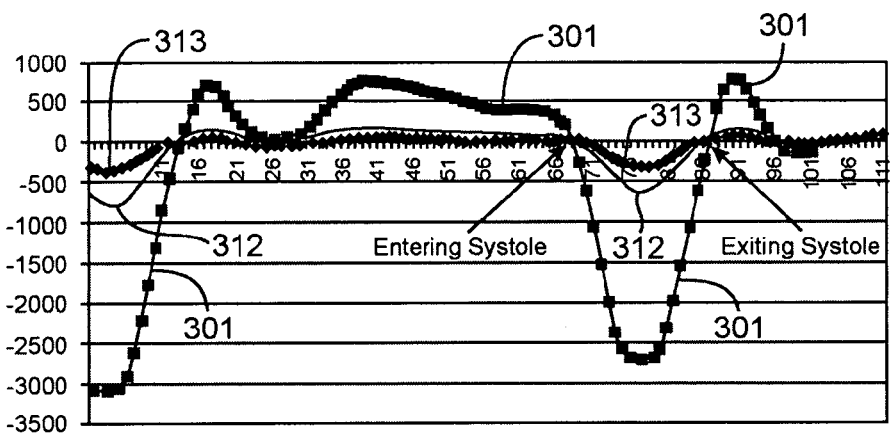

FIG. 3B shows examples of the minimum moving average 301 with a waveform 313 that represents $1/16$ of the sum of the minimum and maximum moving averages of the third stage. FIG. 3B also shows an example of waveform 312 that represents $1/8$ of the sum of the minimum and maximum moving averages of the third stage.

According to one embodiment of the present invention, waveforms 312 and 313 are compared to the minimum moving average waveform 301 at step 205 to identify the systolic period of the pulse oximeter signal. Alternatively, other scaled sums for the minimum and/or maximum moving averages can be used to identify systolic periods in the pulse oximeter signal. The beginning and the end of a systole in signal 301 are identified in FIG. 3B. The period between crossing points of signal 301 and signals 312/313 defines the systolic period.

Figure 3C:
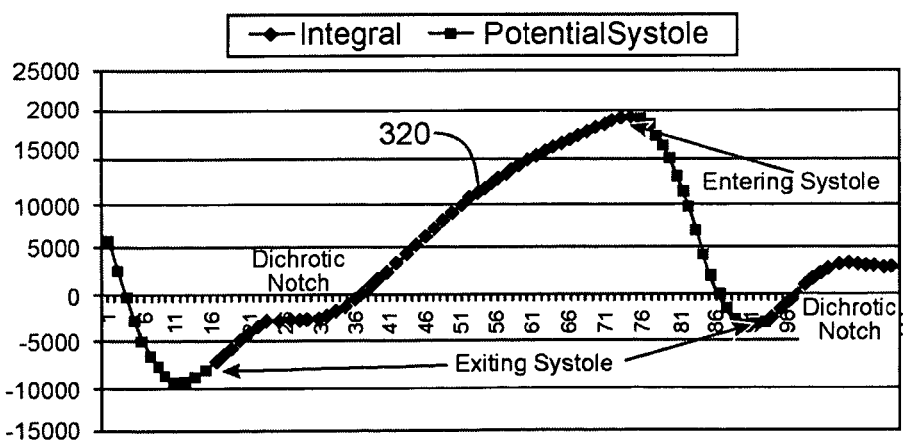

When applied to the original pulse oximeter signal 320, the systolic period identification is shown in FIG. 3C. The systolic period includes the time between the peak (i.e. maximum value) and the subsequent valley (i.e. minimum value) of pulse oximeter signal 320. The actual systolic period is identified in FIG. 3C as well as the dichrotic notch of the next pulse.

After the systolic period has been identified, unique pulse qualification tests based upon typical physiological pulse characteristics are applied to the systole pulse at step 206. The full pulse qualification tests remove false positive systolic detections (e.g., the dichrotic notch) and pulses that have an inadequate signal-to-noise ratio. False positives are portions of the signal that are falsely identified as systolic transitions in step 205. Pulse qualifications are used in step 206 to filter out false positives identified in step 205. The steps of FIG. 2 can be implemented in software or hardware.

Pulse qualification tests qualify cardiac pulses in the pulse oximeter signal. The pulse qualification tests are designed to identify cardiac pulses that have adequate signal-to-noise ratio for use in measuring pulse rate and blood oxygen saturation. The pulse qualification tests can include any number techniques including traditional pulse qualification techniques.

Some examples of pulse qualification tests according to particular embodiments of the present invention are now discussed. The qualifications are comparisons of special pulse characteristics to determined threshold values. For example, the pulse qualifications compare systolic area, width, and number of sub-peaks to fixed thresholds. Diastolic area, width, and number of sub-peaks are compared to thresholds. Systolic area and width are compared to diastolic area and width. Pulse area and width are compared to thresholds. All of the above individually are compared to the last N pulses detected.

Pulses that pass these qualifications can be used to measure pulse rate. To qualify the systolic periods for oxygen saturation calculations, the following additional qualifications are used. The lag/lead time between the infrared and red pulse detection are compared. The pulse size is compared to the N pulses qualified. The statistically significant coefficient of the best-fit line plot of the moving average between the infrared and the red signals is compared to fixed thresholds. The saturation rate-of-change is compared to fixed thresholds. Pulses that pass these additional qualifications can be used to measure oxygen saturation.

After the pulse qualification tests have filtered out false positives, the systolic periods are identified. The systolic periods represent a signal component of the pulse oximeter signal. The signal-to-noise ratio of the pulse oximeter signal is calculated by comparing the strength of the systolic period to the noise component of the pulse oximeter signal.

According to one embodiment, the noise component of a pulse oximeter sensor is calculated in advance using a separate instrument that measures noise in the pulse oximeter signal at various gain values. The measured noise component is then stored in memory for later use. The stored noise component is subsequently compared to the size of the systolic pulse for a particular gain value to determine the signal-to-noise ratio of the pulse oximeter signal.

According to another embodiment, dynamic measurements of the noise of the pulse oximeter system are made. These noise measurements can include electrical noise, ambient noise caused by ambient light, and/or noise (e.g. motion) caused by the patient. The dynamic noise measurement is updated continuously throughout the operation of the pulse oximeter sensor. An updated noise component is continuously compared to the pulse to calculate a more accurate signal-to-noise ratio of the pulse oximeter signal.

Once the signal-to-noise ratio of the pulse oximeter signal has been calculated, a determination is made as whether the signal-to-noise ratio falls within an acceptable range. The acceptable range is selected based on the relative noise component for accurately calculating oxygen saturation and pulse rate. If the ratio is outside the acceptable range, the feedback loop discussed above with respect to FIG. 1 adjusts the LED drive current to bring the signal-to-noise ratio within the acceptable range.

The present invention has the advantage of requiring fewer servo executions to acquire and maintain the oxygen saturation of the signal than many prior art techniques, particularly in the presence of patient motion interference. In many prior art oximeter systems, the LEDs are driven with a large current, and the pulse oximeter signal fills up its entire system dynamic range. The oximeter signal exceeds the system's current dynamic range as soon as the patient starts moving, and the signal is effectively lost (i.e., flat-line, invalid signal). Additional servo executions are required to re-acquire the signal. While the servo is executing, the sensor signal is not available; therefore, the oximeter cannot calculate pulse rate or oxygen saturation data from the pulse oximeter signal.

On the other hand, the LED drive current is substantially reduced in the present invention. The dynamic range is greatly increased relative to the size of the pulse oximeter signal, because the signal has been greatly reduced by cutting back on the LED drive current. The oximeter signal can now move around more within the dynamic range without requiring additional servo executions or changes to the LED settings. In the present invention, the patient can move around vigorously without causing the servo to execute in an attempt to re-acquire the signal. The techniques of the present invention can allow an oximeter system to be much more tolerant of patient motion.

Figure 4:
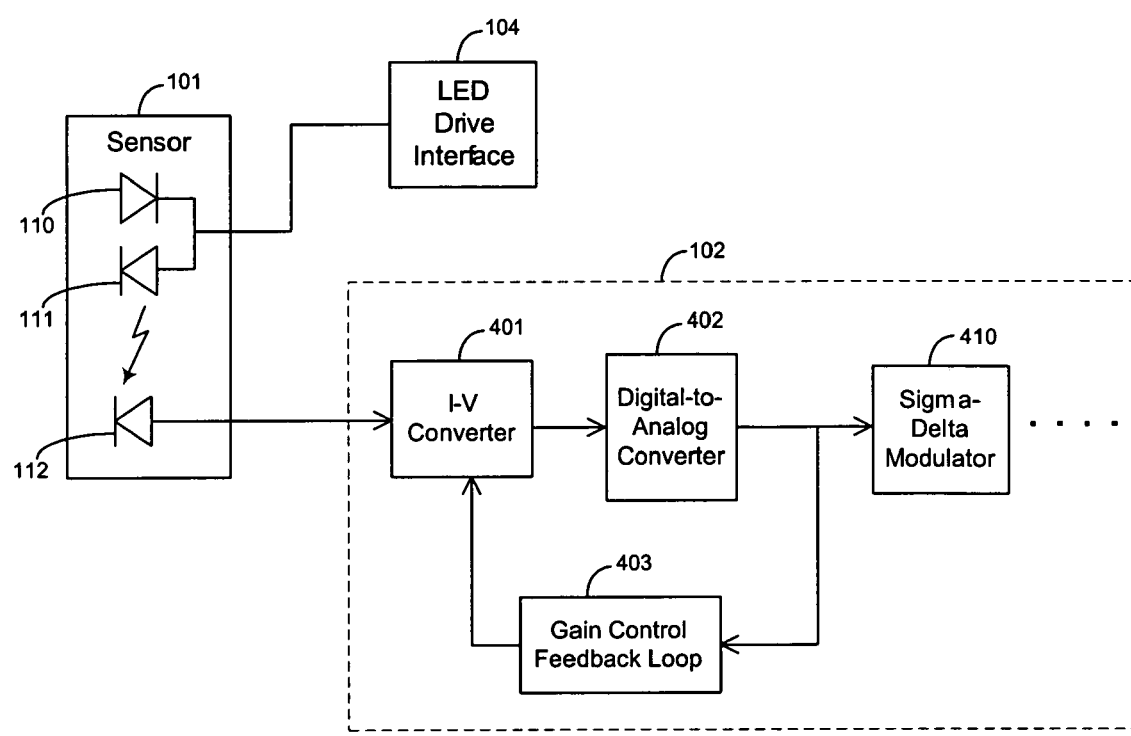
FIG. 4 illustrates a portion of a pulse oximeter system with a transimpedance amplifier, a sigma-delta modulator, an analog-to-digital converter, and a gain control feedback loop according to an embodiment of the present invention.

Pulse detection block 102 can include a transimpedance (I-V) amplifier or converter 401 that converts a current signal from photodetector 112 to a voltage signal as shown in FIG. 4. Ambient light in the environment adds a component of DC bias into the pulse oximeter signal. This DC bias shifts the pulse oximeter signal higher, closer to the rail of the dynamic range of the transimpedance amplifier.

According to an embodiment of the present invention, an analog-to-digital (A-to-D) converter 402 samples the output signal of transimpedance amplifier 401 during a time when either LED 110–111 is on or off to provide a continuous, real-time measurement of the ambient light and or noise that gets into sensor 101. This feature can also be used to provide information on the magnitude of the signal at the output of A-to-D converter 402.

The information about the signal magnitude from A-to-D converter 402 is fed back through gain control feedback loop 403 and used to choose an appropriate gain for transimpedance amplifier 401. For example, gain control feedback loop 403 causes the transimpedance gain of transimpedance amplifier 401 to increase or decrease to reduce and/or accommodate the effect of the environmental DC bias on the signal. This real-time measurement can also be used for determining a sensor-off condition, measuring electrical and optical noise, detecting transients in the signal, and detecting patient motion.

During the normal operation of the sensor, the LEDs can be pulsed on and off in any desired manner to provide the continuous (multiplexed), real-time measurement of the ambient light and other noise sources. For example, one red and one infrared LED can be alternately turned on and off in the following manner: red LED on and infrared LED off, then red LED off and infrared LED on, then both LEDs off, then red LED on and infrared LED off, etc, repeating in this sequence. As another example, one red and one infrared LED can be alternately turned on and off as follows: red LED on and infrared LED off, then both LEDs off, then red LED off and infrared LED on, then both LEDs off, then red LED on and infrared LED off, etc. repeating in this sequence. These patterns are examples that are not intended to limit the scope of the present invention.

Sigma-delta modulator 410 also receives the output signal of the transimpedance amplifier 402. Modulator 410 demodulates the signal from the photodetector into separate red and infrared components. The demodulation function can be performed in the digital domain using a software or firmware program run by a microcontroller. Further details of a Multi-Bit ACD With Sigma-Delta Modulation are discussed in commonly assigned, co-pending U.S. Patent Application 2005/0184895, to Ethan Petersen et al., filed concurrently herewith, which is incorporated by reference herein.

As will be understood by those of skill in the art, the present invention could be embodied in other specific forms without departing from the essential characteristic thereof. Accordingly, the foregoing description is intended to be illustrative, but not limiting, on the scope of the invention which is set forth in the following claims.

For example, the components in pulse detection block 102 that are shown in FIG. 4 can be implemented in systems other than pulse oximeter systems. These components can reduce the effect of noise in signals from other types of sensors as well.

What is claimed is:

1. A pulse oximeter system comprising:
    a drive interface that controls drive current of light emitting elements in a pulse oximeter sensor; and
    a feedback loop coupled around the pulse oximeter sensor and the drive interface that dynamically adjusts the drive current of the light emitting elements based on results of a comparison between a signal-to-noise ratio of a pulse oximeter signal and a threshold, wherein the feedback loop comprises:
    a pulse detection block that calculates a moving average of a derivative of the pulse oximeter signal to generate a first output, calculates a moving average of the first output to generate a second output, calculates a moving average of the second output to generate a third output, and identifies a moving minimum and a moving maximum of the third output in order to determine the signal-to-noise ratio; and
    a comparator that performs the comparison of the signal-to-noise ratio of the pulse oximeter signal to the threshold, wherein the pulse oximeter signal is generated by a photodetector in the pulse oximeter sensor.

2. The pulse oximeter system as defined in claim 1 wherein the feedback loop causes the drive current of the light emitting elements to decrease if the signal-to-noise ratio of the pulse oximeter signal is greater than a maximum threshold, and the feedback loop causes the drive current of the light emitting elements to increase if the signal-to-noise ratio of the pulse oximeter signal is less than a minimum threshold.

3. The pulse oximeter system as defined in claim 1 wherein the pulse detection block compares the moving minimum and the moving maximum of the third output to a scaled sum of the moving minimum and the moving maximum of the third output to generate a fourth output that identifies a systolic period.

4. The pulse oximeter system as defined in claim 3 wherein the pulse oximeter system filters out false positives from the fourth output using pulse qualification tests to generate a signal component of the pulse oximeter signal.

5. The pulse oximeter system as defined in claim 4 wherein the pulse oximeter system compares systolic area, width, and number of sub-peaks in the fourth output to first thresholds; compares diastolic area, width, and number of sub-peaks in the fourth output to second thresholds; compares systolic area and width to diastolic area and width; and compares pulse area and width to third thresholds.

6. The pulse oximeter system as defined in claim 4 wherein the pulse oximeter system compares systolic area, width, and number of sub-peaks in the fourth output; diastolic area, width, and number of sub-peaks in the fourth output; and pulse area and width to N detected heart pulses.

7. The pulse oximeter system as defined in claim 4 wherein the pulse oximeter system performs additional qualification tests to generate the signal component by comparing the lag/lead time between infrared pulse detection and red pulse detection, comparing pulse size to N qualified pulses, comparing a statistically significant coefficient of a best-fit line plot of a moving average between the infrared and the red signals to thresholds, and comparing a saturation rate-of-change to thresholds.

8. The pulse oximeter system as defined in claim 4 wherein the pulse oximeter system compares the signal component to a determined noise component to calculate the signal-to-noise ratio.

9. The pulse oximeter system as defined in claim 4 wherein the pulse oximeter system compares the signal component to a noise component, the noise component being obtained by a continuously updated measurement of noise in the pulse oximeter signal.

10. The pulse oximeter system as defined in claim 4 wherein the pulse detection block detects and qualifies pulses using CPU, RAM, and ROM efficient algorithms.

11. A method for reducing power consumption in a pulse oximeter sensor, the method comprising:
providing drive current to light emitting elements in the pulse oximeter sensor; and
determining a signal-to-noise ratio of a pulse oximeter signal generated by a photodetector in the pulse oximeter sensor, wherein determining the signal-to-noise ratio of the pulse oximeter signal further comprises:
calculating a moving average of a derivative of the pulse oximeter signal to generate a first output;
calculating a moving average of the first output to generate a second output;
calculating a moving average of the second output to generate a third output; and
identifying a moving minimum and a moving maximum of the third output; and
dynamically adjusting the drive current of the light emitting elements based on results of a comparison between the signal-to-noise ratio of the pulse oximeter signal and a threshold, wherein dynamically adjusting the drive current of the light emitting elements comprises:
increasing the drive current provided to the light emitting elements if the signal-to-noise ratio of the pulse oximeter signal is less than a minimum threshold; and
decreasing the drive current provided to the light emitting elements if the signal-to-noise ratio of the pulse oximeter signal is greater than a maximum threshold.

12. The method as defined in claim 11 wherein determining the signal-to-noise ratio of the pulse oximeter signal further comprises:
comparing the moving minimum and the moving maximum of the third output to a scaled sum of the moving minimum and the moving maximum of the third output to generate a fourth output that identifies a systolic period.

13. The method as defined in claim 12 wherein determining the signal-to-noise ratio of the pulse oximeter signal further comprises:
filtering out false positives from the fourth output using pulse qualification tests to generate a signal component of the pulse oximeter signal.

14. The method as defined in claim 13 wherein determining the signal-to-noise ratio of the pulse oximeter signal further comprises:
comparing the signal component to a determined, noise component to calculate the signal-to-noise ratio.

15. The method as defined in claim 13 wherein determining the signal-to-noise ratio of the pulse oximeter signal further comprises
comparing the signal component to a noise component, wherein the noise component is obtained by a continuously updated measurement of noise in the pulse oximeter signal.

16. A method for identifying systolic transitions in a pulse oximeter signal generated by a pulse oximeter sensor, the method comprising:
calculating a moving average of a derivative of the pulse oximeter signal to generate a first output;
calculating a moving average of the first output to generate a second output;
calculating a moving average of the second output to generate a third output;
identifying a moving minimum and a moving maximum of the third output to a scaled sum of the moving minimum and the moving maximum of the third output to generate a fourth output; and
filtering out false positives in the fourth output using pulse qualification routines to generate a fifth output corresponding to a systolic transition in the pulse oximeter signal.

* * * * *